US008968875B2

(12) United States Patent
Takiff et al.

(10) Patent No.: US 8,968,875 B2
(45) Date of Patent: Mar. 3, 2015

(54) EYEWEAR INCLUDING NITROPHENYL FUNCTIONALIZED BORON PYRROMETHENE DYE FOR NEUTRALIZING LASER THREAT

(76) Inventors: Larry Takiff, Arlington, MA (US); Kevin M. Bardon, Somerville, MA (US); Charles Lysogorski, Essex Junction, VT (US); Oliver Pentenrieder, Essex Junction, VT (US)

( * ) Notice: Subject to any disclaimer, the term of this patent is extended or adjusted under 35 U.S.C. 154(b) by 272 days.

(21) Appl. No.: 13/426,491

(22) Filed: Mar. 21, 2012

(65) Prior Publication Data
US 2013/0252000 A1 Sep. 26, 2013

(51) Int. Cl.
C08K 5/3415 (2006.01)
G02B 1/04 (2006.01)
G02B 5/22 (2006.01)

(52) U.S. Cl.
CPC ... *G02B 5/223* (2013.01); *G02B 1/04* (2013.01); *C08K 5/3415* (2013.01)
USPC ............................ 428/412; 359/885; 524/105

(58) Field of Classification Search
None
See application file for complete search history.

(56) References Cited

U.S. PATENT DOCUMENTS

| | | |
|---|---|---|
| 3,679,788 A | 7/1972 | Kiyono et al. |
| 4,812,142 A | 3/1989 | Brodmann |
| 5,073,313 A | 12/1991 | Umemura et al. |
| 6,348,596 B1 | 2/2002 | Lee et al. |
| 8,486,311 B1 | 7/2013 | Takiff et al. |
| 2004/0221403 A1 | 11/2004 | Pyles et al. |
| 2009/0089942 A1 | 4/2009 | Pyles et al. |
| 2010/0110370 A1 | 5/2010 | Krieg-Kowald et al. |
| 2010/0213356 A1 | 8/2010 | Berginc et al. |
| 2011/0255051 A1* | 10/2011 | McCabe et al. ............... 351/163 |

FOREIGN PATENT DOCUMENTS

EP 1 739 119 A1 1/2007
JP 2010184880 A * 8/2010

OTHER PUBLICATIONS

Machine translation of JP 2010-184880 A, Aug. 2010.*
Gabe et al., Highly sensitive fluorescence probes for nitric oxide based on boron dipyrromethene chromophore-rational design of potentially useful bioimaging fluorescence probe. J Am Chem Soc. Mar. 17, 2004;126(10):3357-67.
Loudet et al., Bodipy dyes and their derivatives: syntheses and spectroscopic properties. Chem Rev. Nov. 2007;107(11):4891-932. Epub Oct. 9, 2007.
Marme et al., Inter- and intramolecular fluorescence quenching of organic dyes by tryptophan. Bioconjug Chem. Nov.-Dec. 2003;14(6):1133-9.
Nierth et al., Anthracene-Bodipy dyads as fluorescent sensors for biocatalytic Diels-Alder reactions. J Am Chem Soc. Mar. 3, 2010;132(8):2646-54. doi: 10.1021/ja9084397.

(Continued)

*Primary Examiner* — Ramsey Zacharia
(74) *Attorney, Agent, or Firm* — Wolf, Greenfield & Sacks, P.C.

(57) ABSTRACT

The embodiments described herein generally relate to compositions and articles including dye compounds having desirable optical properties, and related methods. In some cases, the compositions and articles may possess advantageous optical properties, including various degrees of absorbance, emission, and/or transmission at particular wavelengths or ranges of wavelength. Embodiments described herein may be useful as optical filters in protective eyewear applications.

9 Claims, 6 Drawing Sheets

REV011

REV013

REV050

REV052

REV054

REV055

(56) References Cited

OTHER PUBLICATIONS

Roller et al., The determination of the Förster distance (R0) for phenanthrene and anthracene derivatives in poly(methyl methacrylate) films. J Phys Chem B. Jun. 30, 2005;109(25):12261-9.
Shah et al., Pyrromethene-BF2 complexes as Laser Dyes:1. Heteroat Chem. 1990;1(5):389-99.
Sunahara et al., Design and synthesis of a library of Bodipy-based environmental polarity sensors utilizing photoinduced electron-transfer-controlled fluorescence ON/OFF switching. J Am Chem Soc. May 2, 2007;129(17):5597-604. Epub Apr. 11, 2007.
Tahtaoui et al., Convenient method to access new 4,4-dialkoxy- and 4,4-diaryloxy-diaza-s-indacene dyes: Synthesis and spectroscopic evaluation. J Org Chem. Jan. 5, 2007;72(1):269-72.
Treibs et al., Difluorboryl-Komplexe von Di- and Tripyrrylmethenen. Liebigs Ann Chem. 1968;718:208-23.
Ueno et al., Mechanism-based molecular design of highly selective fluorescence probes for nitrative stress. J Am Chem Soc. Aug. 23, 2006;128(33):10640-1.
Vos De Wael et al., Pyrromethene-BF2, complexes (4,4'-difluoro-4-bora-3a,4a-diaza-s-indacenes). Synthesis and luminescence properties. Reel Trav Chim Pays-Bas. 1977;96:306-9.
Ziessel et al., Boron dipyrromethen dyes: a rational avenue for sensing and light emitting devices. Dalton Trans. Jun. 21, 2006;(23):2913-8. Epub May 3, 2006.
Ziessel et al., Isocyanate-, isothiocyanate-, urea-, and thiourea-substituted boron dipyrromethene dyes as fluorescent probes. J Org Chem. Apr. 14, 2006;71(8):3093-102.
http://en.wikipedia.org/wiki/Bis(2-ethylhexyl)_adipate; printed May 21, 2014.

* cited by examiner

FIG. 1A

REV011

REV013

REV050

REV052

REV054

REV055

EYEWEAR INCLUDING NITROPHENYL FUNCTIONALIZED BORON PYRROMETHENE DYE FOR NEUTRALIZING LASER THREAT

FIELD

Compositions and articles including boron pyrromethene compounds, and related methods, are described.

BACKGROUND

Battlefield lasers are an increasing threat to warfighters. Existing eye protection typically involves the use of broad band dyes at high enough dye levels to be protective against multiple wavelengths, but often allowing too little ambient light transmission (e.g., visible light transmission) for good vision, especially at night and in low-light conditions. Visible light transmission is broken down into photopic luminous transmittance (daytime) and scotopic luminous transmittance (nighttime or low-light conditions). Scotopic luminous transmittance for eye protection incorporating 532 nm and 1064 nm blocking dyes is currently below about 10%, which essentially precludes use of these lenses at low light levels.

SUMMARY

Articles are provided comprising an optical filter including a substantially optically transparent polymer; and a boron pyrromethene compound associated with the polymer, are provided, wherein the boron pyrromethene compound comprises a nitro group.

Compositions comprising boron pyrromethene compounds are also provided. In some embodiments, the compound has the following structure, wherein:

each $R^1$-$R^6$ can be the same or different and each is hydrogen, halo, acyl, carboxyl, cyano, nitro, sulfonate, alkyl, alkenyl, alkynyl, cycloalkyl, cycloalkenyl, heterocyclyl, aryl, heteroaryl, any of which is optionally substituted; and any two of $R^1$-$R^6$ can be joined to form a ring, optionally substituted;

X is N or $CR^7$, wherein $R^7$ is hydrogen, halo, acyl, carboxyl, cyano, nitro, sulfonate, alkyl, alkenyl, alkynyl, cycloalkyl, cycloalkenyl, heterocyclyl, aryl, heteroaryl, any of which is optionally substituted; and $Y^1$ and $Y^2$ can be the same or different and each is halo, acyl, carboxyl, cyano, nitro, sulfonate, any of which is optionally substituted; or $Y^1$ and $Y^2$ are joined to form a ring, optionally substituted.

In some embodiments, the compound includes at least one electron-withdrawing group, such as a nitro group.

Methods for forming, processing, and/or using the compositions and articles described herein are also provided.

Other aspects, embodiments and features will become apparent from the following detailed description when considered in conjunction with the accompanying drawings. The accompanying figures are schematic and are not intended to be drawn to scale. For purposes of clarity, not every component is labeled in every figure, nor is every component of each embodiment shown where illustration is not necessary to allow those of ordinary skill in the art to understand the embodiments described herein. All patent applications and patents incorporated herein by reference are incorporated by reference in their entirety. In case of conflict, the present specification, including definitions, will control.

DETAILED DESCRIPTION

Embodiments described herein may be useful in a wide range of applications, including optical filters and applications provided with optical filters such as eyewear, namely, lenses, eyeglasses, goggles, visors, and the like. For example, articles including compounds described herein may be used as optical filters having the ability to substantially block or absorb emissions having a particular wavelength or that are within a particular wavelength range, while simultaneously allowing other emissions to be transmitted through the article. In one set of embodiments, the article may be capable of blocking or absorbing hazardous laser radiation (e.g., laser radiation at about 532 nm), while simultaneously allowing other visible light to be transmitted through the article. For example, the article may be laser protective eyewear fabricated using a boron pyrromethene compound and an optically transparent, high-strength ballistic material such as polycarbonate. Such embodiments may provide enhanced levels of visible light transmission during daytime and/or nighttime or low-light conditions, excellent protection against common laser threats, and good environmental stability and robustness.

The embodiments described herein generally relate to compositions including dye compounds having desirable optical properties, and related optical filters including such dye compounds to provide protection against light of a particular wavelength (e.g., laser light) without inhibiting vision. Embodiments described herein may possess advantageous optical properties, including various degrees of absorbance, emission, and/or transmission at particular wavelengths or ranges of wavelength. Compositions described herein may be readily synthesized and/or purified, and may exhibit sufficient photochemical and/or thermal stability to be processed, for example, via injection molding.

In some embodiments, the composition exhibits strong light absorbance at particular wavelengths, or ranges of wavelength. For example, the composition may have a strong and narrow absorbance band at a particular wavelength or wavelengths (e.g., about 532 nm), yet have relatively low absorbance at other wavelengths. Such compositions may be useful in applications where selective absorbance of light may be desired, such as optical filters, for example. In one set of embodiments, the composition may be incorporated into eyewear for protection against laser light, as described more fully below. Compositions having a narrow absorbance band may advantageously enhance the transmission of light at other wavelengths.

In one set of embodiments, the composition or article exhibits a strong, narrow absorbance band at or near about 532 nm when exposed to electromagnetic radiation. That is, the compositions may absorb light at or near 532 nm but may allow for high visible light transmission at other wavelengths.

In some embodiments, the composition or article may exhibit an enhancement of one or more components of visible light transmission, such as photopic luminous transmission (e.g., daytime transmittance) and/or scotopic luminous transmittance (e.g., nighttime transmittance). For example, eyewear articles may allow for enhanced vision at night and/or in low-light conditions. In some embodiments, articles including a dye compound as described herein may exhibit a scotopic luminous transmittance (SLT) from about 10% to about 50% when the article has an optical density of about 4 at a selected absorbance wavelength (e.g., 532 nm). In some embodiments, the article may exhibit an SLT of about 10%, about 15%, about 20%, about 25%, about 30%, about 35%, about 40%, about 45%, or about 50%, when the article has an optical density of about 4 at a selected absorbance wavelength. In one set of embodiments, articles including a dye compound as described herein may exhibit an SLT of about 30%, when the article has an optical density of about 4 at a selected absorbance wavelength. In some embodiments, articles including a dye compound as described herein may exhibit photopic luminous transmittance (PLT) of about 30%, about 40%, about 50%, or about 60%, when the article has an optical density of about 4 at a selected absorbance wavelength. In one set of embodiments, articles including a dye compound as described herein may exhibit a PLT of about 40%, when the article has an optical density of about 4 at a selected absorbance wavelength.

In some embodiments, articles including a dye compound as described herein may exhibit a PLT of about 30% and an SLT of about 10%, a PLT of about 40% and an SLT of about 10%, or a PLT of about 50% and an SLT of about 10%, when the article has an optical density of about 4 at a selected absorbance wavelength. In some embodiments, articles including a dye compound as described herein may exhibit a PLT of about 30% and an SLT of about 20%, a PLT of about 40% and an SLT of about 20%, or a PLT of about 50% and an SLT of about 20%, when the article has an optical density of about 4 at a selected absorbance wavelength. In some embodiments, articles including a dye compound as described herein may exhibit a PLT of about 30% and an SLT of about 30%, a PLT of about 40% and an SLT of about 30%, or a PLT of about 50% and an SLT of about 30%, when the article has an optical density of about 4 at a selected absorbance wavelength. In one set of embodiments, articles including a dye compound as described herein (e.g., a boron pyrromethene compound) may exhibit PLT of about 50% and an SLT of about 30%, when the article has an optical density of about 4 at a selected absorbance wavelength.

In some embodiments, the composition or article may be substantially non-fluorescent upon exposure to electromagnetic radiation, i.e., the composition or article may have a quantum yield of fluorescence of about 5% or less when exposed to electromagnetic radiation between about 300 nm and about 600 nm.

Some embodiments provide compositions including a boron pyrromethene compound. (FIG. 1A) In some embodiments, the boron pyrromethene compound may be selected to exhibit one or more of a particular, desired optical property (e.g., absorbance, fluorescence, phosphorescence, chemiluminescence, etc.) upon exposure to electromagnetic radiation. For example, the composition may exhibit a narrow absorbance peak at a particular wavelength, allowing the composition to serve as an optical filter as it absorbs a specific wavelength of light (e.g., harmful laser light) while allowing other light to pass through the composition. In some cases, the boron pyrromethene compound may be appropriately substituted to exhibit a maximum absorbance peak at a particular wavelength upon exposure to electromagnetic radiation. The selection of different substituents on the boron pyrromethene compound may shift the wavelength at which the composition exhibits a maximum absorbance peak, producing optical filters that can absorb/filter light of different wavelengths.

For example, to filter light having relatively shorter wavelengths, the compound may be substituted with one or more electron-poor groups, such as acyl, carboxyl, cyano, nitro, sulfonate, fluoroalkyls, or the like, such that a maximum absorbance peak of the compound is shifted to relatively shorter wavelengths (e.g., blue-shifted). In cases where it is desirable to filter light having relatively longer wavelengths, the compound may be substituted with one or more electron-rich groups, such as amino, hydroxy, alkoxy, acylamino, acyloxy, alkyl, halide, and the like, such that a maximum absorbance peak of the compound is shifted to relatively longer wavelengths (e.g., red-shifted). In some cases, the boron pyrromethene compound may be substituted with a combination of electron-poor and electron-rich groups. The maximum absorbance peak may be a particular peak having the largest intensity in an absorbance spectrum, or, alternatively, the maximum absorbance peak may be a peak in an absorbance spectrum that has at least a defined maximum, but has a smaller intensity relative to other peaks in the absorbance spectrum.

In some embodiments, the boron pyrromethene compound has a maximum absorbance peak between about 400 and about 800 nm. In some embodiments, the boron pyrromethene compound has a maximum absorbance peak, between about 470 and about 800 nm, between about 500 and about 800 nm, or between about 500 and about 650 nm. In some cases, the boron pyrromethene compound has a maximum absorbance peak of about 400, about 425, about 450, about 475, about 500, about 525, about 550, about 575, about 600, about 625, about 650, about 675, about 700, about 725, about 750, about 775, or about 800 nm. In some embodiments, the boron pyrromethene compound has a maximum absorbance peak within about 15 nm, within about 10 nm, within about 5 nm, or within about 2 nm of a particular desired wavelength, as described herein. In some embodiments, the boron pyrromethene compound has a maximum absorbance peak of about 532 nm. In some embodiments, the boron pyrromethene compound has a maximum absorbance peak of about 455 nm.

Some embodiments may involve the use of boron pyrromethene compounds that can selectively filter a specific, narrow band of light while allowing other light to be transmitted so as to not interfere with normal vision. Such compounds may exhibit a relatively narrow absorbance peak. For example, the compound may exhibit a strong absorbance peak at a particular wavelength in the visible spectrum, while minimizing absorbance of light at other wavelengths and maximizing transmission of visible light. Such compounds may be useful, for example, as optical filters.

In some embodiments, optical properties which would interfere with normal vision (e.g., fluorescence emission, light scattering) may be reduced or eliminated. In some cases, the boron pyrromethene compound may be selected to exhibit a relatively low, or substantially no, fluorescence emission upon exposure to electromagnetic radiation in order to improve vision through the optical filter. In some cases, the composition or article has a quantum yield of fluorescence of about 5% or less upon exposure to electromagnetic radiation between about 300 nm and about 600 nm. In some cases, the composition or article has a quantum yield of fluorescence of about 0.01% to about 5%, about 0.01% to about 4%, about 0.01% to about 3%, about 0.01% to about 2%, or about 0.01% to about 1%, upon exposure to electromagnetic radiation between about 300 nm and about 600 nm.

In some cases, a solid article containing a boron pyrromethene compound as described herein may exhibit low or substantially no fluorescence emission upon exposure to electromagnetic radiation. In some cases, a solution containing a boron pyrromethene compound as described herein may exhibit low or substantially no fluorescence emission upon exposure to electromagnetic radiation. In some embodiments, the boron pyrromethene compound may be highly fluorescent in both solution (e.g., a chloroform solution) and in solid form (e.g., in a polycarbonate matrix). In some embodiments, the boron pyrromethene compound may be highly fluorescent in solution but may be substantially non-fluorescent in solid form. In other embodiments, the boron pyrromethene compound may be highly fluorescent in solid form but may be substantially non-fluorescent in solution.

The quantum yield, or fluorescence yield, of a material refers to the ratio of photons emitted through fluorescence to photons absorbed. Those of ordinary skill in the art would be able to select a method for measuring the quantum yield of fluorescence of a material, including comparison of the fluorescence emission of a known standard dye compound with that of a test dye compound. Typically, samples which absorb an essentially identical number of photons are compared, e.g., by comparing samples having essentially identical optical densities at a particular wavelength when exposed to an essentially identical set of conditions (e.g., electromagnetic radiation having the same wavelength) or by adjusting the fluorescence emission data to correct for any differences in absorbance value and/or concentration between the standard and the test samples. For example, the fluorescence emission intensity of a test dye in film may be adjusted to account for any differences in absorbance value and concentration when compared to the reported fluorescence emission intensity of known standard dye. The quantum yield of fluorescence of the test dye in film may then be calculated based on the difference between fluorescence emission intensities of the standard dye and test dye in film, as well as the reported quantum yield of fluorescence for the standard dye in film.

Without wishing to be bound by any theory, reduced fluorescence in some boron pyrromethene compounds may be attributed to an intramolecular electron transfer reaction, i.e., electron transfer from one portion of the molecule to another portion of the molecule, that quenches fluorescence. For example, the compound may include one portion including electron-rich groups and another portion including electron-poor groups, creating a molecular dipole moment and resulting in a reduced fluorescence, or substantially no fluorescence, upon exposure to electromagnetic radiation.

In some embodiments, the boron pyrromethene compound may be appropriately functionalized to impart other desired characteristics (e.g., surface properties) to the compound. For example, the boron pyrromethene compound may include substituents that can alter or improve properties such as compatibility with a medium (e.g., solubility, stability), photostability, and/or thermal stability. In some cases, the boron pyrromethene compound may comprise functional groups selected to possess an affinity for a surface. In some embodiments, the polymer comprises a sterically bulky group that may aid in preserving the optical properties of the compound, even in the solid state. Some embodiments may involve boron pyrromethene compounds substituted with various alkyl groups, for example, to enhance solubility or compatibility of the compound in a hydrophobic medium and/or to tailor the maximum absorbance peak of the compound.

Figure 1A:
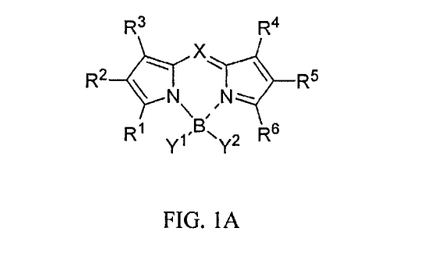
FIG. 1 shows (a) a boron pyrromethene structure, (b) some examples of boron pyrromethene compounds as described herein, and (c) an example of eyewear in which boron pyrromethene compounds may be incorporated.

The boron pyrromethene compound may have a structure as shown in FIG. 1A, wherein:

each $R^1$-$R^6$ can be the same or different and each is hydrogen, halo, acyl, carboxyl, cyano, nitro, sulfonate, alkyl, alkenyl, alkynyl, cycloalkyl, cycloalkenyl, heterocyclyl, aryl, heteroaryl, any of which is optionally substituted; and any two of $R^1$-$R^6$ can be joined to form a ring, optionally substituted;

X is N or $CR^7$, wherein $R^7$ is hydrogen, halo, acyl, carboxyl, cyano, nitro, sulfonate, alkyl, alkenyl, alkynyl, cycloalkyl, cycloalkenyl, heterocyclyl, aryl, heteroaryl, any of which is optionally substituted; and $Y^1$ and $Y^2$ can be the same or different and each is halo, acyl, carboxyl, cyano, nitro, sulfonate, any of which is optionally substituted; or $Y^1$ and $Y^2$ are joined to form a ring, optionally substituted.

In some embodiments, the boron pyrromethene compound comprises at least one electron-withdrawing group. For example, the electron-withdrawing group may be halo, acyl, carboxyl, cyano, nitro, or sulfonate. In one set of embodiments, the boron pyrromethene compound comprises at least one, at least two, or at least three nitro groups.

In some embodiments, $R^1$, $R^2$, $R^3$, $R^4$, $R^5$, and $R^6$ are each independently alkyl; X is $CR^7$; and $Y^1$ and $Y^2$ are each halo (e.g., fluoro). In some cases, $R^1$, $R^2$, $R^3$, $R^4$, $R^5$, and $R^6$ are each independently methyl, ethyl, or propyl.

In some embodiments, $R^1$, $R^3$, $R^4$, and $R^6$ are each independently alkyl; $R^2$ and $R^5$ can be the same or different and each is halo, acyl, carboxyl, cyano, nitro, sulfonate, or fluoroalkyl; X is $CR^7$; and $Y^1$ and $Y^2$ are each halo (e.g., fluoro).

In some embodiments, $R^1$, $R^3$, $R^4$, and $R^6$ are each independently methyl, ethyl, or propyl; and $R^2$ and $R^5$ are each nitro.

In some embodiments, $R^7$ is an optionally substituted aryl. In some cases, $R^7$ may be an aryl group substituted with 1-5 substituents selected from the group consisting of acyl, carboxyl, cyano, nitro, or sulfonate. In some embodiments, $R^7$ may be an aryl group substituted with at least one nitro group.

In some embodiments, $Y^1$ and $Y^2$ are each fluoro.

Some examples of boron pyrromethene compounds include, but are not limited to, the following structures, In some cases, the article includes a boron pyrromethene compound in combination with one or more additional components. For example, the article may include a boron pyrromethene compound associated with a polymer material (e.g., polycarbonate). In some embodiments, the boron pyrromethene compound may be dispersed on or within at least a portion of the polymer. In some cases, the compound is formed as a coating on the polymer.

Some embodiments may provide an article including an optical filter including a substantially optically transparent polymer, and a boron pyrromethene compound associated with the polymer. In one particular embodiment, the article comprises polycarbonate and a boron pyrromethene compound dispersed on and/or throughout the polycarbonate. The optical filter may be a film or coating applied to the article, such as eyewear, or at least a portion of the article may be formed of the optical filter. Representative of the latter arrangement is molding an eyeglass or goggle lens from a polymer and a boron pyrromethene compound associated with the polymer.

In one set of embodiments, the article may comprise a polycarbonate and a boron pyrromethene compound including a catechol group associated with the polycarbonate, and may exhibit a combination of high absorbance at or near 532 nm, high visible light transmission, high thermal stability, and low fluorescence.

It should be understood that boron pyrromethene compounds are described by way of example only, and other, similar compounds may be useful in the context of the embodiments described herein. For example, boron azapyrromethene compounds, porphyrin compounds, boron furanopyrrole compounds (e.g., Keio dyes), and the like may also be used.

Some embodiments may involve the use of a combination of various dye compounds, each compound having an absorbance at a different wavelength. For example, the article or composition may include a mixture of different boron pyrromethene compounds, each compound having a different chemical structures and an absorbance at a different wavelength. In another example, the article or composition may include a mixture of different dye compounds, including boron pyrromethene compounds and other compounds, where each compound exhibits an absorbance at a different wavelength. Such embodiments may be used to tailor the optical properties of the composition or article, allowing for selective absorption at various wavelengths.

Various polymers may be suitable for use in the methods described herein. In some embodiments, the polymer may be an optical plastic such as polycarbonate. Other examples include, but are not limited to, polyethylene, polypropylene, poly(vinyl chloride), poly(methyl methacrylate), poly(vinyl benzoate), poly(vinyl acetate), polystyrene, cellulose, poly(vinyl pyrrolidinone), polyamide, polyacrylamide, epoxys, silicones, poly(vinyl butyral), polyurethane, nylons, polyacetal, polycarbonate, polyesters, polyethers, cyclic olefin polymers, copolymers such as polyester-polycarbonate, acrylonitrile-butadiene-styrene (ABS), crosslinked polymers such as polystyrene-poly(divinyl benzene), polyacrylamide-poly(methylenebisacrylamide), polybutadiene copolymers, combinations thereof, and the like.

Boron pyrromethene compounds may be synthesized using various methods known to those of skill in the art. Generally, a pyrrole species and an aldehyde species may react via a condensation reaction (e.g., an acid-catalyzed condensation reaction) to form a pyrromethene ligand, which may be then be reacted with a boron-containing species to form the boron pyrromethene compound. Various pyrrole species, aldehyde species, and a boron-containing species containing a range of substituents are readily accessible and known to those of skill in the art. Further modification of the boron pyrromethene compound may be carried out using known methods, including substitution of ligands attached to the boron atom and/or modification of functional groups on the pyrromethene ligand.

The compositions and articles described herein may be produced using various methods known in the art. For example, the boron pyrromethene compound may be combined with a solvent (e.g., an oil), and may then be add to a polymer (e.g., in pellet form, in powder form, etc.). The mixture may be shaken and/or stirred for a period of time to substantially uniformly associate the boron pyrromethene onto, within, and/or throughout the polymer. The concentration of boron pyrromethene in the solvent may be varied to suit a particular application. In some embodiments, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg of boron pyrromethene compound per 0.5 mL solvent may be used. Additionally, the ratio, by weight, of boron pyrromethene compound to polymer may also be varied to suit a particular application. In some embodiments, the ratio of boron pyrromethene compound to polymer may be about 1:1, about 1:2, about 1:3, about 1:4, about 1:5, about 1:10, about 1:20, about 1:30, about 1:40, about 1:50, or less, by weight. In one set of embodiments, the ratio of dye compound to polymer is about 1:5, by weight. Those of ordinary skill would be able to select the appropriate amounts of dye compound, solvent, and polymer suitable for use in a particular application.

In an illustrative embodiment, the method may be carried out using about 25 mg of boron pyrromethene compound and 100 g polycarbonate pellet in 0.5 mL of solvent. In some cases, the solvent is an oil such as bis(2-ethylhexyl)adipate (BEHA).

Boron pyrromethene compounds may also be coated onto a solid substrate by methods known to those skilled in the art, such as dip coating, rod coating, slot coating, blade coating, spin coating, and the like. For example, the compound may be combined with a solvent, and the resulting solution may be used to coat a solid substrate (e.g., a polymer substrate). Removal of the solvent (e.g., by evaporation or drying) may then produce the coated article.

The resulting material may be further processed to form articles, including molded articles. In some cases, the material may be processed using extrusion processing methods or thermoforming methods known to those skilled in this art. In some cases, the material may be processed via injection molding. In some cases, the material may be processed via thermoforming. In one set of embodiments, the polymer-boron pyrromethene material may be introduced into an extruder wherein the mixture is melted and homogenized in the barrel of the molding machine. The molten material may then be extruded either through an extrusion die or into a mold to form the finished product.

In the compounds and compositions described herein, the term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, a straight chain or branched chain alkyl may have 30 or fewer carbon atoms in its backbone, and, in some cases, 20 or fewer. In preferred embodiments, a straight chain or branched chain alkyl has 12 or fewer carbon atoms in its backbone (e.g., $C_1$-$C_{12}$ for straight chain, $C_3$-$C_{12}$ for branched chain), and more preferably 6 or fewer, and even more preferably 4 or fewer. Likewise, preferred cycloalkyls have from 3-10 carbon atoms in their ring structure, and more preferably have 5, 6 or 7 carbons in the ring structure. Examples of alkyl groups include, but are not limited to, methyl, ethyl, propyl, isopropyl, cyclopropyl, butyl, isobutyl, tert-butyl, cyclobutyl, hexyl, cyclohexyl, and the like.

The terms "alkenyl" and "alkynyl" refer to unsaturated aliphatic groups analogous in length and possible substitution to the alkyls described above, but that contain at least one double or triple bond respectively.

As used herein, the term "halo" or "halide" designates —F, —Cl, —Br, or —I.

The terms "carboxyl group," "carbonyl group," and "acyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." The term "carboxylate" refers to an anionic carboxyl group. In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

The term "aryl" refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups. In some cases, the The terms "heteroaryl" refers to aryl groups including at least one heteroatom as a ring atom. Suitable heteroatoms include oxygen, sulfur, nitrogen, phosphorus, and the like. Heteroaryls include, for example, thiophene, benzothiophene, thianthrene, furan, tetrahydrofuran, pyran, isobenzofuran, chromene, xanthene, phenoxathiin, pyrrole, pyrrolidine, imidazole, pyrazole, pyrazine, isothiazole, isoxazole, pyridine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, and the like. The heteroaryl ring can be optionally substituted at one or more positions with such substituents as described herein. In some cases, the heteroaryl may be bonded to a compound via a heteroatom ring atom (e.g., nitrogen). In some cases, the heteroaryl may be bonded to a compound via a carbon ring atom.

The terms "amine" and "amino" are art-recognized and refer to both unsubstituted and substituted amines, e.g., a moiety that can be represented by the general formula: N(R')(R")(R'") wherein R', R", and R'" each independently represent a group permitted by the rules of valence. An example of a substituted amine is benzylamine.

Any of the above groups may be optionally substituted. As used herein, the term "substituted" is contemplated to include all permissible substituents of organic compounds, "permissible" being in the context of the chemical rules of valence known to those of ordinary skill in the art. It will be understood that a "substituted" compound is a stable compound, e.g., one which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of the embodiments described herein, the heteroatoms such as nitrogen may have hydrogen substituents and/or any permissible substituents of organic compounds described herein which satisfy the valencies of the heteroatoms.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, carboxamido, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl, and the like.

EXAMPLES

Example 1

The following example describes a general synthetic procedure for nitro-substituted boron pyrromethene compounds. A solution of pyrrole (2 eq.) and aldehyde (1 eq.) were dissolved in anhydrous dichloromethane under an Ar atmosphere. One drop of trifluoroacetic acid (TFA) was added and the solution was stirred at room temperature overnight. Upon complete consumption of the aldehyde, 2,3-dichloro-5,6-dicyano-1,4-benzoquinone (DDQ) (1 eq) was added and stirring was continued for 15 min. The reaction mixture was washed several times with water, the organic portion was recovered, dried over $Na_2SO_4$, filtered and carried on to the next step without further purification.

The dipyrromethene solution in dichloromethane was thoroughly sparged with Ar while stirring, then diisopropylethylamine (10 eq) was added. The reaction mixture was sparged while stirring for an additional 20 min, at which point it was carefully treated with boron trifluoride diethyl etherate solution ($BF_3.OEt_2$) (14 eq.) under inert atmosphere and allowed to stir vigorously as such at room temperature overnight. Upon completion, the reaction mixture was stirred with an equal volume of water for 30 min, then the organic portion was washed several times more, collected, dried over $Na_2SO_4$, filtered and adsorbed onto silica powder. The material was then subjected to flash column chromatography (FCC) using a hexane/ethyl acetate gradient to elute the difluoro-BODIPY dye.

For the pyrrolic nitration, the suitable difluoro-BODIPY dye (1 eq.) was dissolved in concentrated nitric acid at 0° C. and stirred for 1.5 h. After this time, a large excess of water was added to the reaction mixture to precipitate the crude product. This material was then subjected to FCC using a hexane/ethyl acetate gradient to elute the trinitro product.

Example 2

The following example describes a general method for preparation of films containing boron pyrromethene compounds as described herein. A stock solution of polycarbonate dissolved in chloroform (10% m/m) was made. The dry boron pyrromethene material was dissolved in a small volume of the 10% polycarbonate/chloroform solution (5-10 mg/mL), homogenized and then distributed onto a polyester film substrate. The boron pyrromethene solution was immediately pulled unidirectionally at a steady, moderate rate using a #18 wire-wound rod (RD Specialties, NY) to produce a uniform film coating. Upon drying, spectral characterization and analysis was conducted.

Example 3

Figure 1B:
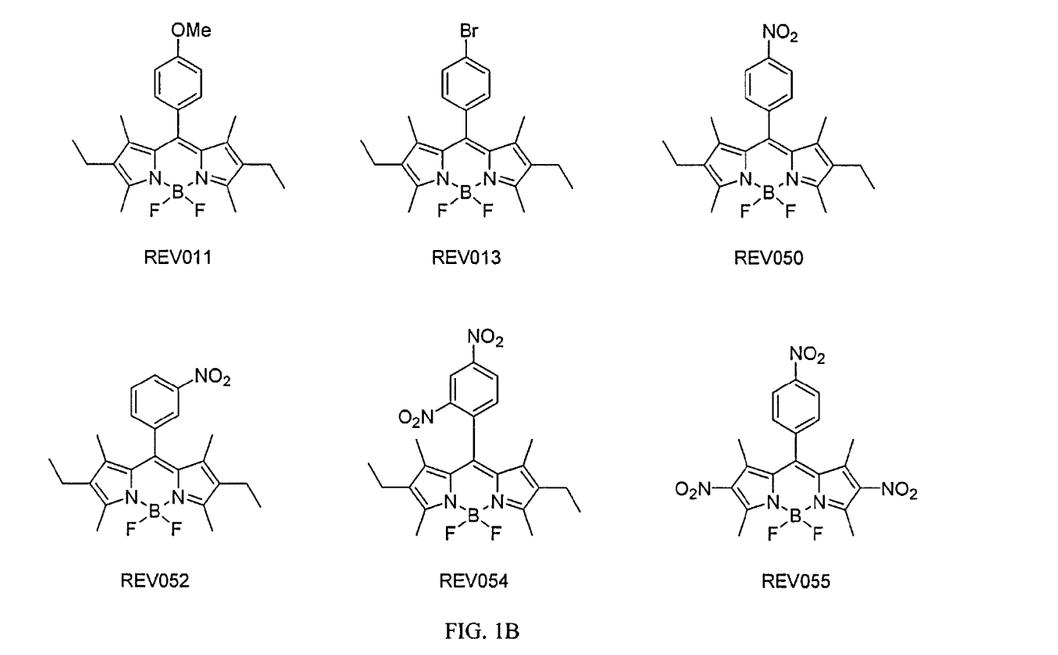
Figure 1C:
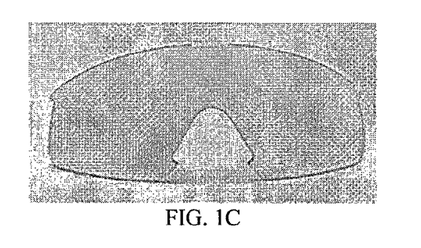

A series of boron pyrromethene compounds, as shown in FIG. 1B, was synthesized as described in Example 3, and the optical properties of the compounds were evaluated. FIG. 1B shows the structures for various non-nitrated boron pyrromethene dyes and nitro-containing boron pyrromethene dyes utilized in this example.

Figure 2:
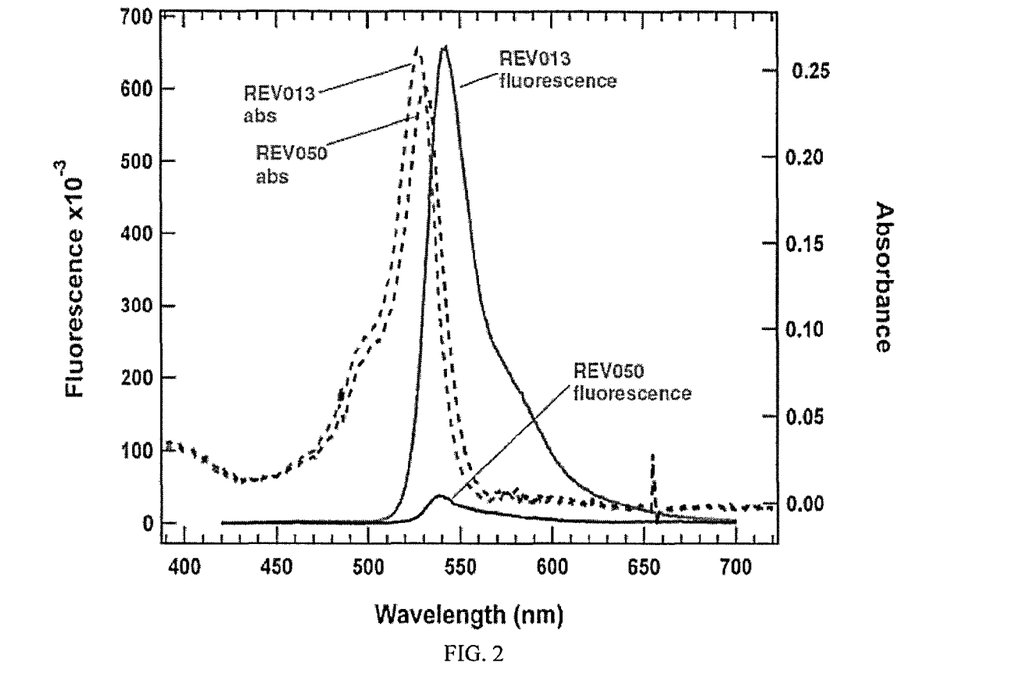
FIG. 2 shows the absorbance spectra and fluorescence emission for a non-nitro-containing boron pyrromethene compound (REV013) and a nitro-containing boron pyrromethene compound (REV050) in solution.
Figure 3:
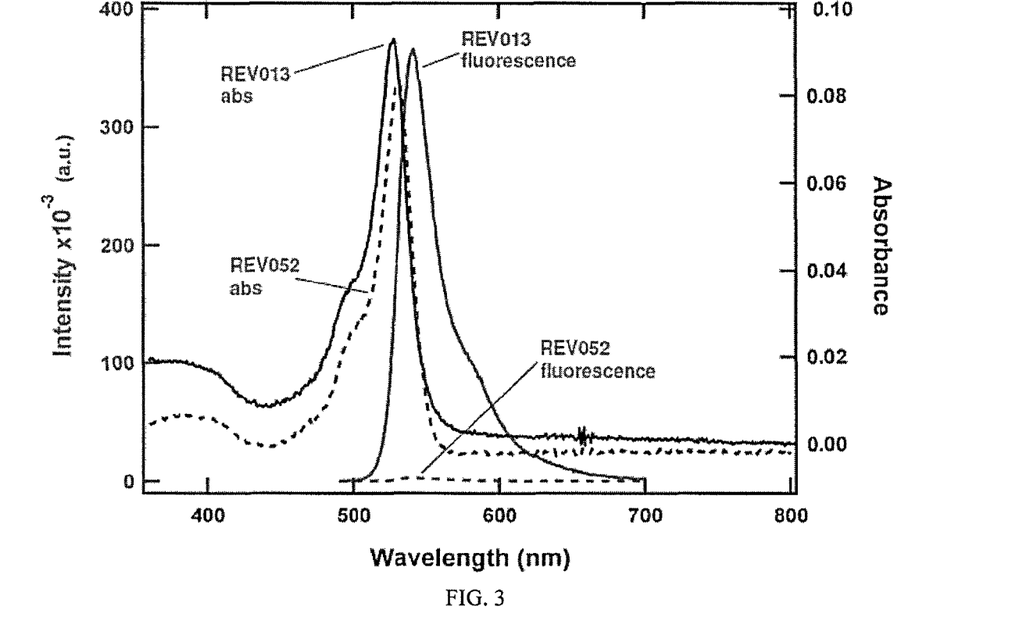
FIG. 3 shows the absorbance spectra and fluorescence emission for a non-nitro-containing boron pyrromethene compound (REV013) and a nitro-containing boron pyrromethene compound (REV052) in solution.
Figure 4:
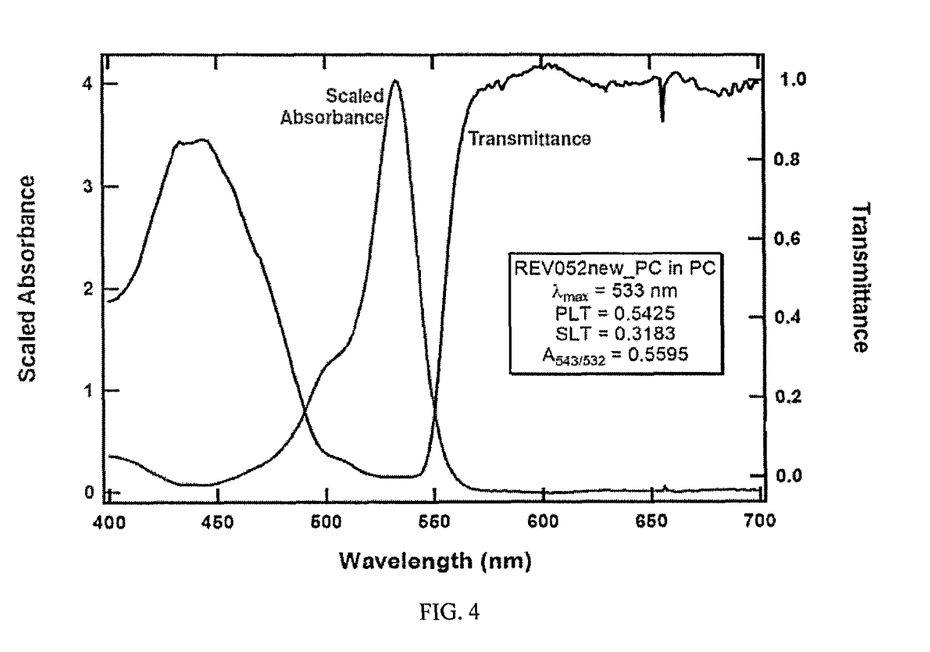
FIG. 4 shows the absorbance and transmittance spectra for a nitro-containing boron pyrromethene compound (REV052) in polycarbaonte.

FIG. 2 shows the absorbance spectra and fluorescence emission for REV013 and REV050 in solution, while FIG. 3 shows the absorbance spectra and fluorescence emission for REV013 and REV052 in solution. Both nitro-containing dyes, REV050 and REV052, showed markedly decreased fluorecence relative to the non-nitrated dye REV013, with REV050 showing only 1.9% fluorescence relative to that of REV013. As shown in FIG. 4, REV052 has low fluorecence and strong absorbance at 533 nm, with an SLT of about 32%.

Figure 5:
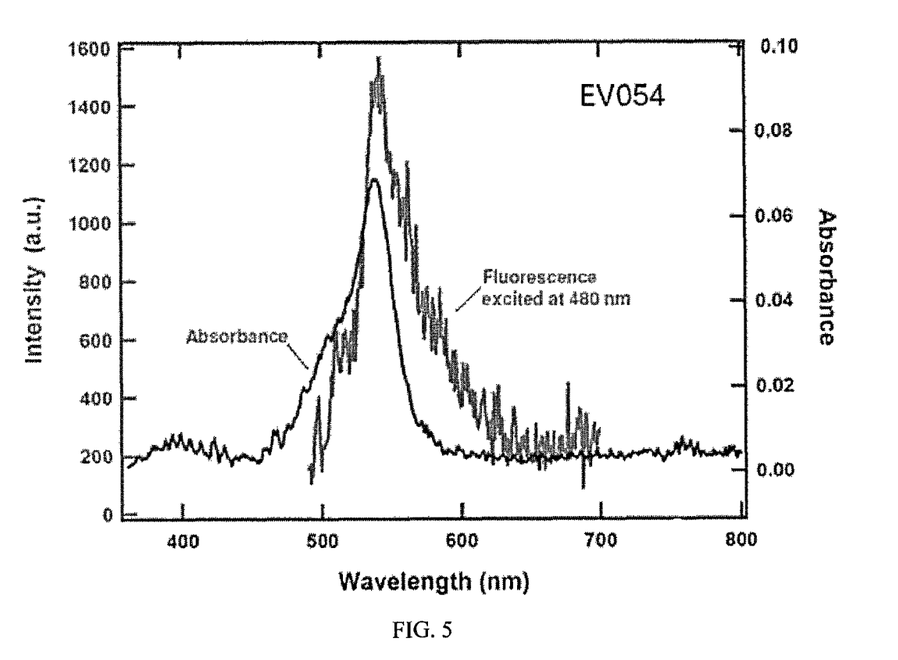
FIG. 5 shows the absorbance spectrum and fluorescence emission spectrum (excited at 480 nm) of another nitro-containing dye (REV054) which contains two nitro groups, in a solution of dichloromethane.

FIG. 5 shows the absorbance spectrum and fluorescence emission (excited at 480 nm) of another nitro-containing dye, REV054, which contains two nitro groups, in a solution of dichloromethane.

Figure 6:
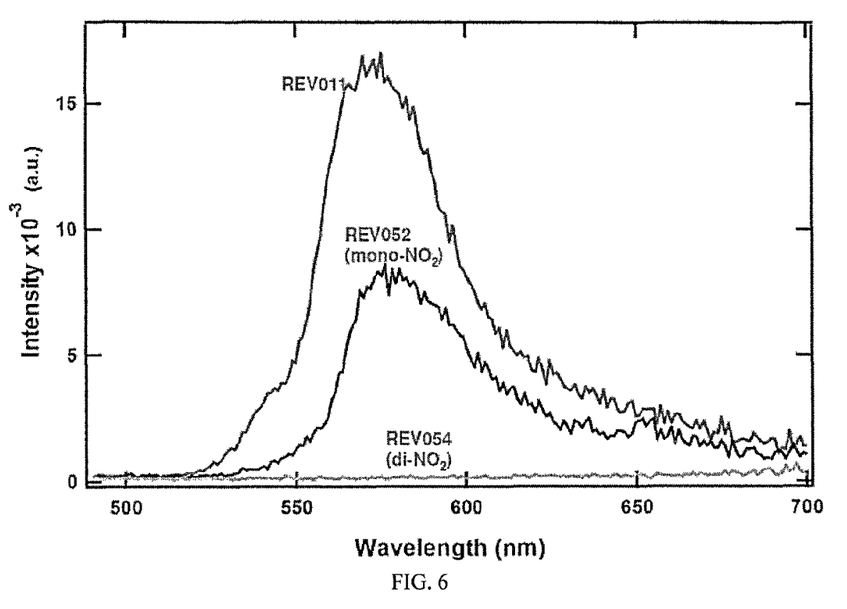
FIG. 6 shows the fluorecence spectra for polycarbonate films containing a non-nitro-containing boron pyrromethene (REV011), a mono-nitrated boron pyrromethene (REV052), and a di-nitrated boron pyrromethene (REV054), when excited at 480 nm.

FIG. 6 shows the fluorecence spectra for polycarbonate films containing a non-nitro-containing boron pyrromethene (REV011), a mono-nitrated boron pyrromethene (REV052), and a di-nitrated boron pyrromethene (REV054), when excited at 480 nm. The increase in the number of nitro groups was shown to decrease the fluorescence.

Figure 7:
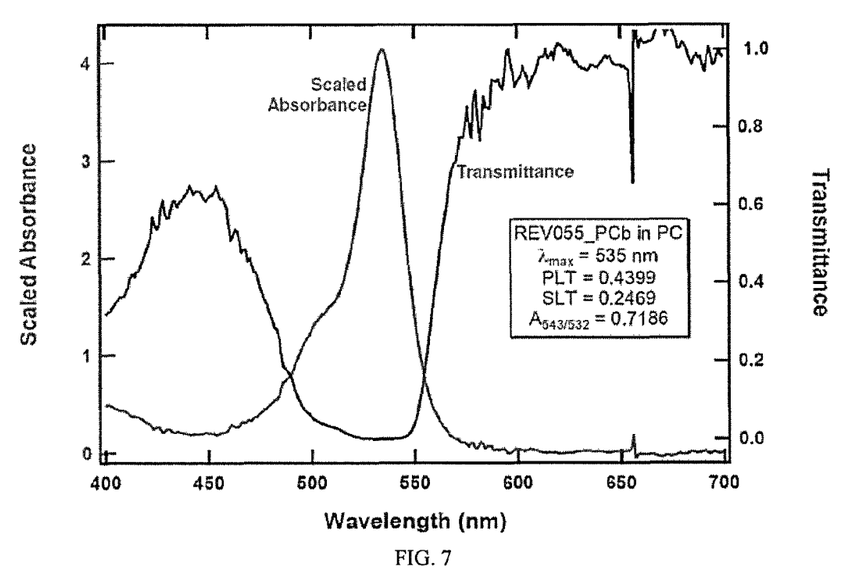
FIG. 7 shows the absorbance and transmittance spectra for a nitro-containing boron pyrromethene compound (REV055) in polycarbonate.

FIG. 7 shows the absorbance and transmittance spectra for a nitro-containing boron pyrromethene compound (REV055) in polycarbaonte. The tri-nitrated REV055 compound exhibits strong absorbance and essentially no fluorescence at 535 nm, wi than SLT valur of about 25%.

Figure 8:
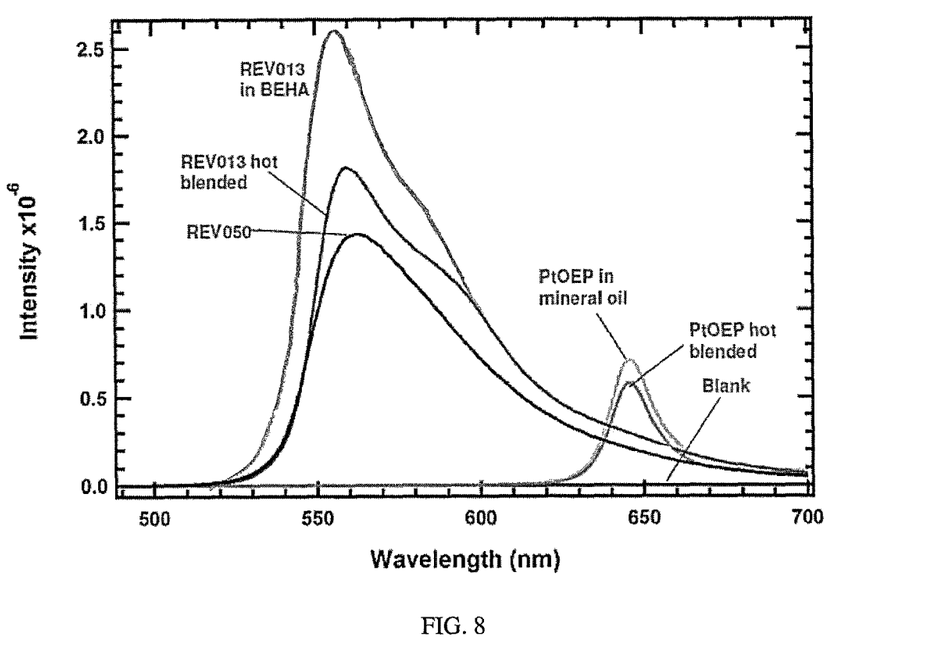
FIG. 8 shows the fluorescence spectra for molded polycarbonate plaques containing either a non-nitro-containing boron pyrromethene compound (REV013), a nitro-containing boron pyrromethene compound (REV050), or PtOEP in either mineral oil, BEHA, or in a hot blend. The molded plaque containing nitrited REV50 was shown to exhibit a reduced fluorescence relative to the non-nitro-containing REV013.

FIG. 8 shows the fluorescence spectra for molded polycarbonate plaques (50 mm squares, 2.2 mm thickness) containing either a non-nitro-containing boron pyrromethene compound (REV013), a nitro-containing boron pyrromethene compound (REV050), or a known dye, PtOEP, in either mineral oil, BEHA, or in a hot blend. The molded plaque containing nitrited REV50 was shown to exhibit a reduced fluorescence relative to the non-nitro-containing REV013.

Fluorescence quantum yields for the dye-containing films were estimated by comparing reported quantum yield of fluorescence for reference dye-containing films (see Prieto, J. B. et al., J. of Luminescence 2007, 126, 833-837, for representative dye-film data) with spectral measurements for the dye-containing films described herein. By correlating UV-vis absorbances with the fluorescence emission intensities of the various films, approximate quantum yields of fluorescence for the dye-containing films were calculated. The quantum yield of fluorescence for previous boron pyrromethene dyes in polymer film has been reported to be in the range of about 25% to about 75%, depending on particular dye, polymer matrix, and concentrations used, with the majority falling within a range of 30-60%.

Figure 9:
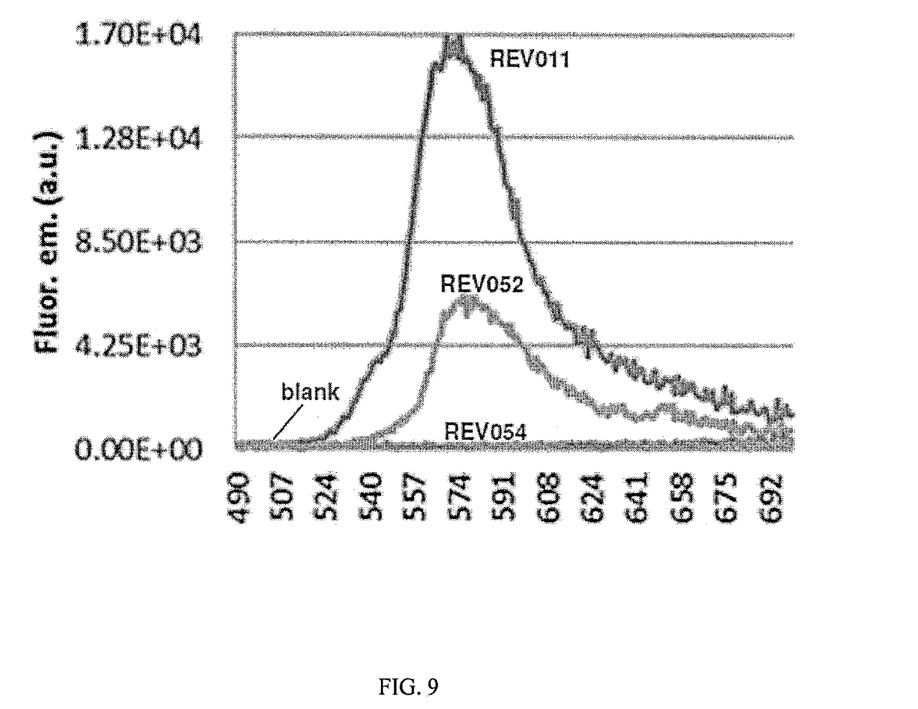
FIG. 9 shows the fluorescence emission spectra of boron pyrromethene dyes in polycarbonate film when excited at 480 nm, where the dyes include 0-3 nitro groups.

In this example, the fluorescence emission intensity of a non-nitro-containing boron pyrromethene (REV013) in polycarbonate film was compared to the fluorescence emission intensities of the nitro-containing boron pyrromethene dyes (REV050, REV052, REV054, REV055) in polycarbonate film, correcting for absorbance values and concentrations. FIG. 9 shows representative fluorescence emission spectra for a blank polycarbonate film, and polycarbonate films including a non-nitro-containing containing boron pyrromethene dye, REV011, or a nitro-containing boron pyrromethene dye (REV052 or REV054).

The boron pyrromethene dyes including one nitro group (REV050 and REV052) exhibited fluorescence emission quenching of approximately ⅓. Factoring this data into the reported range of quantum yields of fluorescence for previous boron pyrromethene dyes, all of which do not contain nitro groups, in polymer film, the expected quantum yield of fluorescence range for the mono-nitrated dyes was calculated to be 10-20% (i.e., ⅓ of the reported range of quantum yields of fluorescence for boron pyrromethene dyes, 30-60%. Boron pyrromethene dyes including two or three nitro groups (REV054, REV055) exhibited fluorescence emission quenching at least 50 times greater that of the mono-nitrated dyes. The emission of REV054 was even shown to overlap with that of a polycarbonate film blank. (FIG. 9) Thus, the quantum yields of fluorescence of these dyes were calculated to fall in a range of 0% to 1%.

Having thus described several aspects of some embodiments of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed:

1. An article, comprising:
an optical filter including a substantially optically transparent polymer; and
a boron pyrromethene compound associated with the polymer, wherein the boron pyrromethene compound comprises a nitro group;
wherein the boron pyrromethene compound has the following structure, wherein:
each $R^1$-$R^6$ can be the same or different and each is hydrogen, halo, acyl, carboxyl, cyano, nitro, sulfonate, alkyl, alkenyl, alkynyl, cycloalkyl, cycloalkenyl, heterocyclyl, aryl, heteroaryl, any of which is optionally substituted; and any two of $R^1$-$R^6$ can be joined to form a ring, optionally substituted;
X is N or $CR^7$, wherein $R^7$ is hydrogen, halo, acyl, carboxyl, cyano, nitro, sulfonate, alkyl, alkenyl, alkynyl, cycloalkyl, cycloalkenyl, heterocyclyl, aryl, heteroaryl, any of which is optionally substituted; and
$Y^1$ and $Y^2$ can be the same or different and each is halo, acyl, carboxyl, cyano, nitro, sulfonate, any of which is optionally substituted; or $Y^1$ and $Y^2$ are joined to form a ring, optionally substituted.

2. An article as in claim 1, wherein the boron pyrromethene compound is dispersed on or within the polymer or formed as a coating on the polymer.

3. An article as in claim 1, wherein the boron pyrromethene compound has a maximum absorption peak between about 400 nm and about 800 nm.

4. An article as in claim 1, wherein the boron pyrromethene compound has a maximum absorption peak at about 532 nm.

5. An article as in claim 1, wherein $R^7$ is an aryl group substituted with at least one nitro group.

6. An article as in claim 5, wherein $Y^1$ and $Y^2$ are each fluoro.

7. An article as in claim 1, wherein the substantially optically transparent polymer is polycarbonate.

8. An article as in claim 1, wherein the optical filter is included in eyewear.

9. An article as in claim 8, wherein the eyewear includes a lens, goggle, eyeglasses, or visor.

* * * * *